United States Patent
Nukui (10) Patent No.: US 9,020,220 B2
(45) Date of Patent: Apr. 28, 2015

(54) X-RAY COMPUTED TOMOGRAPHY SCANNER, DOSE CALCULATION METHOD, AND PROGRAM

(71) Applicant: GE Medical Systems Global Technology Company, LLC, Waukesha, WI (US)

(72) Inventor: Masatake Nukui, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 253 days.

(21) Appl. No.: 13/659,242

(22) Filed: Oct. 24, 2012

(65) Prior Publication Data

US 2013/0108130 A1 May 2, 2013

(30) Foreign Application Priority Data

Oct. 28, 2011 (JP) .................................. 2011-237695

(51) Int. Cl.
  *G06K 9/00* (2006.01)
  *A61B 6/00* (2006.01)

(52) U.S. Cl.
  CPC ................. *A61B 6/542* (2013.01); *A61B 6/488* (2013.01); *A61B 6/583* (2013.01)

(58) Field of Classification Search
  USPC .................................................. 382/128–134
  See application file for complete search history.

(56) References Cited

U.S. PATENT DOCUMENTS

| | | | |
|---|---|---|---|
| 6,650,729 B2 | 11/2003 | Braess et al. | |
| 6,801,647 B1 | 10/2004 | Arakawa | |
| 7,627,079 B2 | 12/2009 | Boone | |
| 8,009,804 B2 | 8/2011 | Siljamaki et al. | |
| 8,270,760 B2 | 9/2012 | Miao et al. | |
| 2006/0078083 A1* | 4/2006 | Nishide et al. | 378/16 |
| 2006/0126911 A1* | 6/2006 | Bohm et al. | 382/132 |
| 2007/0049785 A1* | 3/2007 | Pekar et al. | 600/1 |
| 2007/0053480 A1* | 3/2007 | Nishide et al. | 378/4 |
| 2008/0091388 A1 | 4/2008 | Failla et al. | |
| 2008/0234571 A1* | 9/2008 | Hay et al. | 600/425 |
| 2008/0292055 A1* | 11/2008 | Boone | 378/97 |
| 2008/0315110 A1 | 12/2008 | Iwatschenko-Borho et al. | |
| 2009/0022268 A1* | 1/2009 | Kudo | 378/15 |
| 2010/0228116 A1 | 9/2010 | Lu et al. | |
| 2013/0108130 A1* | 5/2013 | Nukui | 382/131 |
| 2013/0136227 A1* | 5/2013 | Ishihara | 378/19 |

FOREIGN PATENT DOCUMENTS

| | | | |
|---|---|---|---|
| JP | 2004105382 A | 4/2004 |
| JP | 2004195121 | 7/2004 |
| JP | 2006026417 A | 2/2006 |
| JP | 2007054372 A | 3/2007 |
| JP | 2008148886 A | 7/2008 |

* cited by examiner

*Primary Examiner* — Alex Liew
(74) *Attorney, Agent, or Firm* — Armstrong Teasdale LLP (57) ABSTRACT

An X-ray CT apparatus is provided. The X-ray CT apparatus includes an estimation device configured to estimate a feature quantity that relates to one of image quality and a pixel value of an image obtained by performing an X-ray CT scan on a imaging target under a predetermined scan condition, wherein the feature quantity has a correlative relationship with a dose that is based on data obtained from X-ray imaging performed on the imaging target before a main scan, and a calculation device configured to calculate a dose for the imaging target for a case when an X-ray CT scan is performed under a desired setup scan condition, the dose calculated based on the estimated feature quantity and the correlative relationship between feature quantity and dose.

16 Claims, 10 Drawing Sheets

X-RAY COMPUTED TOMOGRAPHY SCANNER, DOSE CALCULATION METHOD, AND PROGRAM

CROSS REFERENCE TO RELATED APPLICATIONS

This application claims the benefit of Japanese Patent Application No. 2011-237695 filed Oct. 28, 2011, which is hereby incorporated by reference in its entirety.

BACKGROUND OF THE INVENTION

The present invention relates to an X-ray computed tomography apparatus, a dose calculation method, and a program thereof.

Generally, an X-ray CT apparatus has functions that calculate and display a dose value for an imaging target based on the size of the imaging target or predetermined scan conditions.

The dose calculation uses dose measurement reference values resulting from actually imaging columnar acrylic phantoms. Two types of phantoms are used as the reference. One type of phantom is 16 cm in diameter and is intended for an infant or adult head. The other is 32 cm in diameter and is intended for an adult body.

Generally, the X-ray CT apparatus selects the measurement reference value for a correspondingly sized phantom based on information about a subject such as distinction between an adult and an infant and imaging locations. The X-ray CT apparatus multiplies the measurement reference value by a factor (weight) based on predetermined scan conditions to calculate a dose. In this manner, the dose is calculated in consideration of imaging target sizes (see for example, the second to fourth paragraphs of JP-A No. 2004-195121).

Phantom sizes are limited to the above-mentioned two types though imaging targets might be sized variously. The same dose might be calculated for a large person and a small person if they use the same phantom to be applied and the same predetermined scan conditions such as a tube voltage, a tube current, X-ray exposure time, and a helical pitch for helical scanning That is, the dose might not appropriately reflect an imaging target size and might not be calculated correctly.

For this reason, there is a demand to more effectively reflect imaging target sizes on dose calculation performed in an X-ray CT apparatus.

BRIEF DESCRIPTION OF THE INVENTION

In a first aspect, an X-ray CT apparatus is provided. The X-ray CT apparatus includes an estimation device for estimating a feature quantity that relates to one of image quality and a pixel value of an image which is obtained by performing X-ray CT scan on a imaging target under a predetermined scan condition and that having correlative relationship with a dose, based on data obtained from X-ray imaging performed on the imaging target before main scan, and a calculation device for calculating a dose for the imaging target for the case when X-ray CT scan is performed under a desired setup scan condition, based on the feature quantity estimated by said estimation device and the predetermined scan condition with referring the preliminary obtained relationship between feature quantity and dose.

In a second aspect, the X-ray CT apparatus according to the first is provided, wherein the relationship being a relationship under the predetermined condition, and wherein the calculation device references the relationship under the predetermined condition, specifies a dose corresponding to a feature quantity estimated by the estimation device, multiplies the specified dose by a factor according to the desired scan condition, and calculates a dose for the imaging target when X-ray CT scan is performed under the desired scan condition.

In a third aspect, the X-ray CT apparatus according to the second aspect is provided, wherein the calculation device multiplies the specified dose by a factor based on the desired scan condition and a desired gain and calculates the dose for the imaging target for the case when X-ray CT scan is performed under the desired scan condition.

In a fourth aspect, the X-ray CT apparatus according to the third aspect is provided, wherein the gain is determined so as to decrease a difference between a dose calculated by the X-ray CT scan and a dose calculated by another X-ray CT scan under substantially the same condition.

In a fifth aspect, the X-ray CT apparatus according to any one of the first through fourth aspects is provided, wherein the feature quantity is an index indicative of an image noise level.

In a sixth aspect, the X-ray CT apparatus according to the fifth aspect is provided, wherein the index is one of variance and standard deviation for pixel values associated with a tomographic image for the imaging target.

In a seventh aspect, the X-ray CT apparatus according to the fifth or sixth aspect is provided, wherein the data is obtained from scout scan on the imaging target.

In an eighth aspect, the X-ray CT apparatus according to any one of the first through fourth aspects is provided, wherein the feature quantity is an index indicating a value converted into a section area of an object made of one of acrylics and other predetermined materials so as to provide an equal dose under the same condition from a section area of the imaging target.

In a ninth aspect, the X-ray CT apparatus according to the eighth aspect is provided, wherein the index is a total of standardized pixel values associated with a tomographic image for the imaging target.

In a tenth aspect, the X-ray CT apparatus according to the eighth or ninth aspect is provided, wherein the data is obtained from one of helical scout scan and axial scout scan on the imaging target.

In an eleventh aspect, the X-ray CT apparatus according to the eighth or ninth aspect is provided, wherein the data is obtained from past X-ray CT scan on the imaging target.

In a twelfth aspect, the X-ray CT apparatus according to any one of the first through eleventh aspects is provided, wherein the relationship is obtained from actual X-ray CT scan on a plurality of columnar phantoms with different diameter.

In a thirteenth aspect, a dose calculation method is provided. The does calculation method includes a first step of estimating a feature quantity that relates to one of image quality and a pixel value of an image which is obtained by performing X-ray CT scan on a imaging target under a predetermined scan condition and that having correlative relationship with a dose, based on data obtained from X-ray imaging performed on the imaging target before main scan, and a second step of calculating a dose for the imaging target for the case when X-ray CT scan is performed under a desired setup scan condition, based on the feature quantity estimated by the first step and said predetermined scan condition with referring said preliminary obtained relationship between feature quantity and dose.

In a fourteenth aspect, the dose calculation method according to the thirteenth aspect is provided, wherein the relationship is a relationship under the predetermined condition, and wherein the second step references the relationship under the predetermined condition, specifies a dose corresponding to a feature quantity estimated by the first step, multiplies the specified dose by a factor according to the desired scan condition, and calculates a dose for the imaging target when X-ray CT scan is performed under the desired scan condition.

In a fifteenth aspect, the dose calculation method according to the thirteenth aspect is provided, wherein the second step multiplies the predetermined dose by a factor based on the desired scan condition and a desired gain and calculates the dose for the imaging target for the case when X-ray CT scan is performed under said desired scan condition.

In a sixteenth aspect, the dose calculation method according to the fifteenth aspect is provided, wherein the gain is determined so as to decrease a difference between a dose calculated by the X-ray CT scan and a dose calculated by another X-ray CT scan under substantially the same condition.

In a seventeenth aspect, the dose calculation method according to any one of the thirteenth through sixteenth aspects is provided, wherein the feature quantity is an index indicative of an image noise level.

In an eighteenth aspect, the dose calculation method according to any one of the thirteenth through sixteenth aspects is provided, wherein the feature quantity is an index indicating a value converted into a section area of an object made of one of acrylics and other predetermined materials so as to provide an equal dose under the same condition from a section area of the imaging target.

In a nineteenth aspect, the dose calculation method of any one of the thirteenth through eighteenth aspects is provided, wherein the relationship is obtained from actual X-ray CT scan on a plurality of columnar phantoms with different diameters.

In a twentieth aspect, a program is provided. The program allows a computer to function as an estimation device for estimating a feature quantity that relates to one of image quality and a pixel value of an image which is obtained by performing X-ray CT scan on a imaging target under a predetermined scan condition and that having correlative relationship with a dose, based on data obtained from X-ray imaging performed on the imaging target before main scan, and a calculation device for calculating a dose for the imaging target for the case when X-ray CT scan is performed under a desired setup scan condition based on the feature quantity estimated by the estimation device and the predetermined scan condition with referring the preliminary obtained relationship between feature quantity and dose.

For example, the "predetermined scan condition" may include a tube voltage for the X-ray tube and a dose. The dose may be represented as "mAs" that is defined as the product of a tube current (mA) in milliamperes for an X-ray tube and the X-ray exposure time (s) in seconds.

For example, the "factor" may represent a weight coefficient that is defined through the use of a tube voltage for the X-ray tube and a dose.

The "scout scan" is performed before the main scan using a lower-dose X-ray beam than the main scan. An example of the "scout scan" provides an imaging system that radiates a lower-dose X-ray beam than the main scan while straightly moving an X-ray source relative to an imaging target without rotating the X-ray source. Another example thereof provides an imaging system according to a helical scan or an axial scan using a lower-dose X-ray beam.

The systems and methods according to the above-mentioned aspects specify the feature quantity associated with the image quality or the pixel value of an image correlative to a dose in accordance with the setup scan condition and calculates the dose with reference to the relationship between the dose and the feature quantity. It is possible to provide successive or multistage values used as references for the calculation and calculate a dose that more accurately reflects the size of an imaging target.

DETAILED DESCRIPTION OF THE INVENTION

Figure 1:
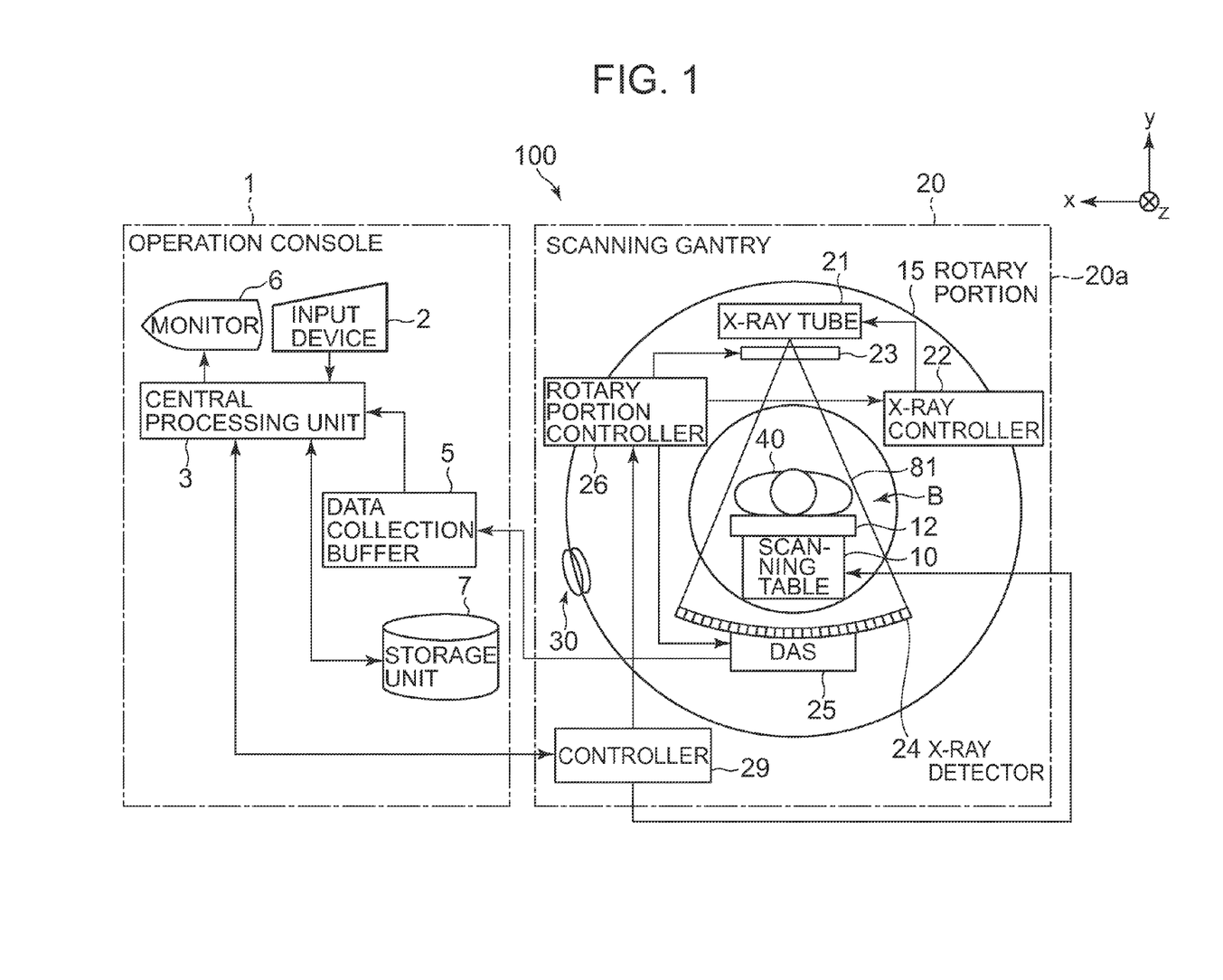
FIG. 1 schematically shows a configuration of an exemplary X-ray CT apparatus.

Exemplary embodiments will be described herein.
(First Embodiment)
FIG. 1 schematically shows a configuration of an X-ray CT apparatus according to the embodiment. An X-ray CT apparatus 100 includes an operation console 1, an scanning table 10, and a apparatus gantry 20.

The operation console 1 includes an input device 2, a central processing unit 3, a data collection buffer 5, a monitor 6, a storage unit 7. The input device 2 accepts inputs from an operator. The central processing unit 3 controls components for imaging a subject and processes data for generating images. The data collection buffer 5 collects data acquired at the apparatus gantry 20. The monitor 6 displays images. The storage unit 7 stores programs and data.

The scanning table 10 includes a cradle 12 that supports a subject 40 and conveys it to an opening of the apparatus gantry 20. A motor contained in the scanning table 10 vertically and horizontally moves the cradle 12. The following description defines the z direction as a body axis direction of the subject 40, that is, a linear movement direction of the cradle 12; the y direction as a vertical direction; and the x direction as a horizontal direction perpendicular to the z direction and the y direction.

The apparatus gantry 20 includes a rotary portion 15 and a body portion 20a that rotatably supports the rotary portion 15. The rotary portion 15 includes an X-ray tube 21, an X-ray controller 22, a collimator 23, an X-ray detector 24, a data acquisition system (DAS) 25, and a rotary portion controller 26. The X-ray controller 22 controls the X-ray tube 21. The collimator 23 collimates an X-ray beam 81 generated from the X-ray tube 21. The X-ray detector 24 detects the X-ray beam 81 that transmits the subject 40. The DAS 25 collects output from the X-ray detector 24 by converting the output into projection data. The rotary portion controller 26 controls the X-ray controller 22, the collimator 23, and the DAS 25. The body portion 20a includes a controller 29 that exchanges control signals with the operation console 1 and the scanning table 10. The rotary portion 15 and the body portion 20a are electrically connected to each other via a slip ring 30.

Figure 2:
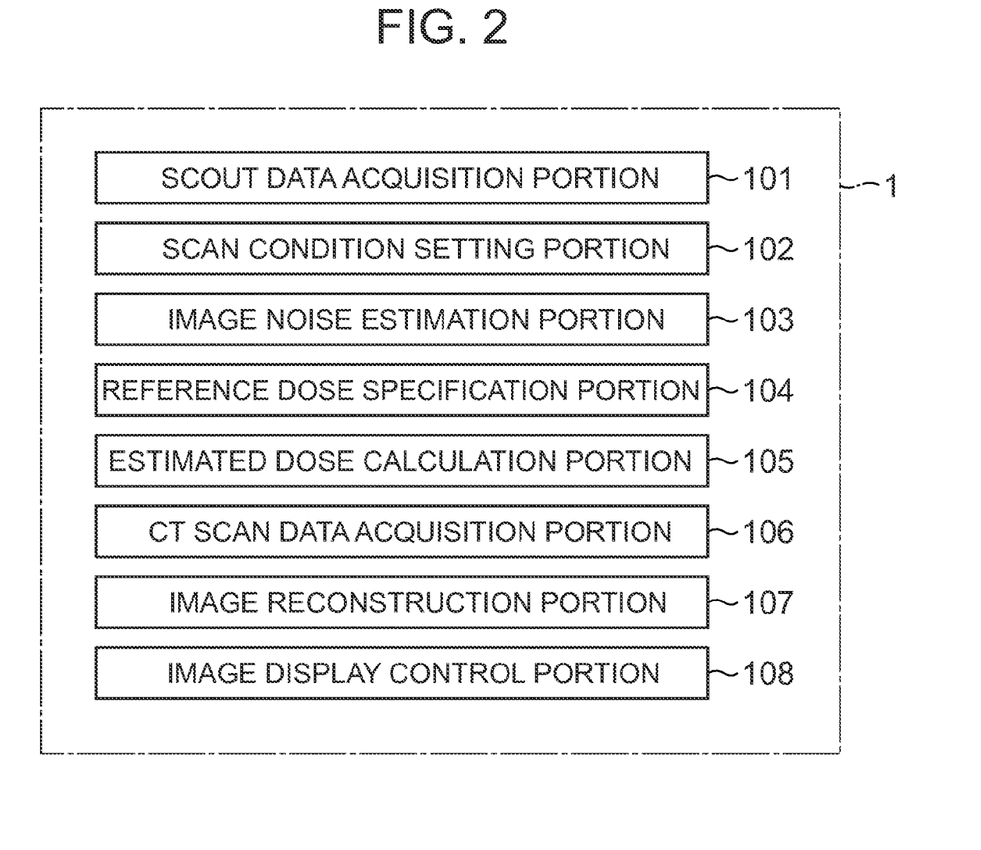
FIG. 2 is a function block diagram showing portions related to scanning performed in the X-ray CT apparatus according to a first embodiment.
Figure 3:
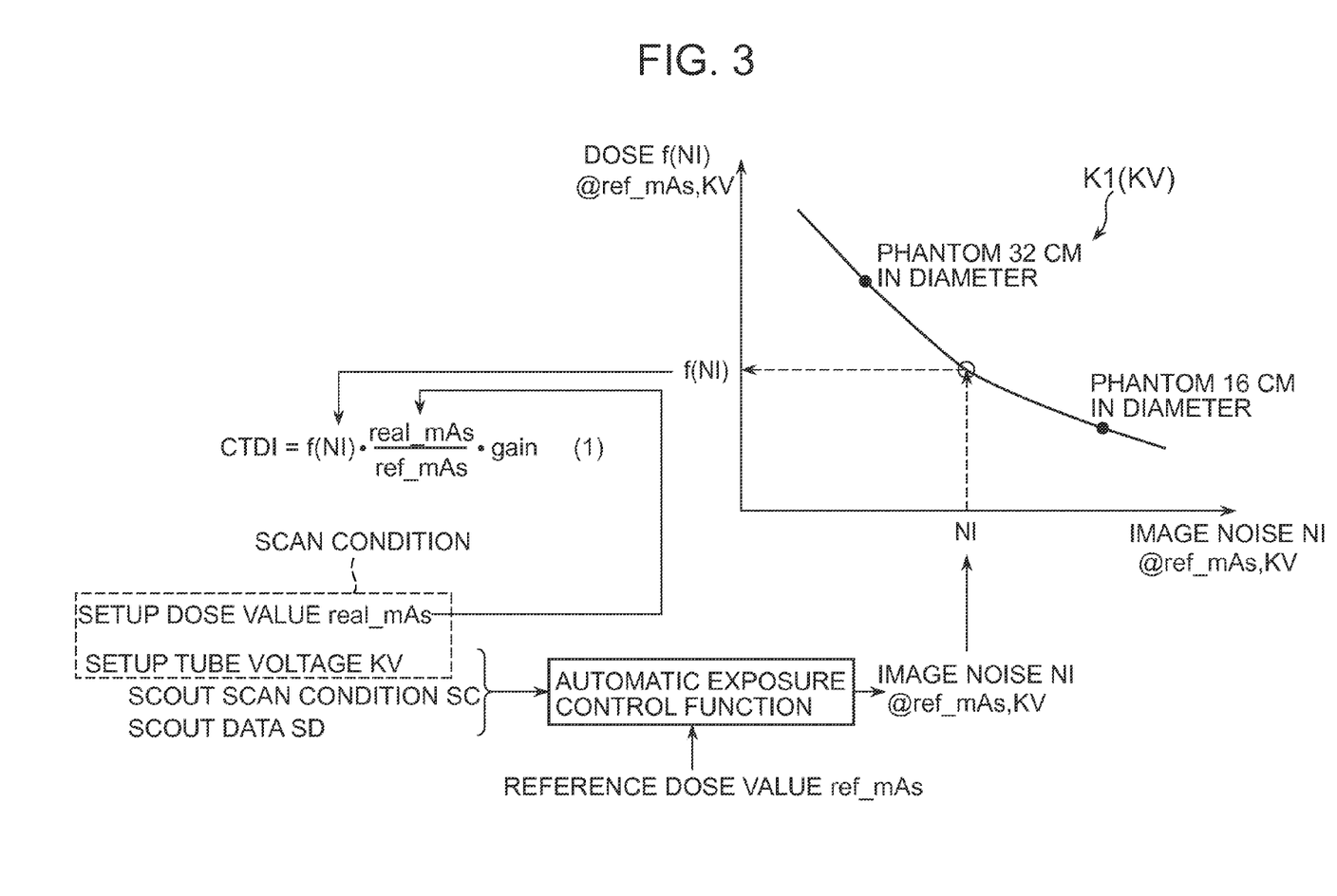
FIG. 3 is a flowchart showing a flow of operations on the X-ray CT apparatus according to the first embodiment.

FIG. 2 is a function block diagram showing portions related to scanning performed in the X-ray CT apparatus according to the first embodiment. FIG. 3 schematically shows a dose calculation method according to the first embodiment.

As shown in FIG. 2, the X-ray CT apparatus according to the embodiment includes a scout data acquisition portion 101, a scan condition setting portion 102, an image noise estimation portion 103 (estimation device), a reference dose specification portion 104 (calculation device), an estimated dose calculation portion 105, a CT scan data acquisition portion 106, an image reconstruction portion 107, and an image display control portion 108.

The scout data acquisition portion 101 controls the scanning table 10 and the apparatus gantry 20 and acquires scout data PS while performing scout scan on an imaging portion (imaging target) of the subject 40 under a predetermined scout scan condition SC. The scout scan is preliminarily performed before the main scan. To perform the scout scan, for example, the subject 40 or the apparatus gantry 20 is moved in the z direction while the X-ray tube 21 is positioned at a predetermined view angle. An X-ray beam with the dose lower than the main scan is radiated to the subject 40 to acquire projection data. For example, the scout scan may be equivalent to a helical scan that uses a lower-dose X-ray beam than the main scan.

The scan condition setting portion 102 configures a predetermined scan condition used for the main scan in accordance with operator operations. The scan condition includes scan parameters such as a scan range, a tube voltage and a tube current for the X-ray tube, the time required to rotate the gantry one turn, and a helical pitch for the helical scan if applicable. These scan parameters determine a setup dose real_mAs (see FIG. 3) that is used to scan an imaging target and is expressed as a product of a setup tube voltage KV, the tube current, and the X-ray exposure time.

The image noise estimation portion 103 estimates an index value NI indicating an image noise level of an image. The index value NI results from scanning an imaging portion under the condition that a tube voltage is set to the setup tube voltage KV and a dose (mAs) is set to a predetermined reference dose ref_mAs. For example, the image is equivalent to a tomographic image corresponding to the representative slice within a predetermined scan range. The predetermined reference dose ref_mAs is equivalent to 100 [mA·S], for example. The setup tube voltage KV is equivalent to 120 [kV], for example.

The image noise estimation portion 103 estimates the index value NI for an image noise using functions of the CT automatic exposure control (CT-AEC) based on the setup tube voltage KV, the scout scan condition SC, and the scout data SD.

The CT automatic exposure control can find a modulation curve for the tube current corresponding to the tube voltage equivalent to the setup tube voltage KV based on the setup tube voltage KV, the scout scan condition SC, the scout data SD, and an index value of the desired image noise. For example, the tube current may be available in the body axis direction or the rotation axis direction and is used as a scan condition for acquiring an image corresponding to the desired image noise.

Accordingly, the use of the algorithm for the CT automatic exposure control can reversely find the index value NI for an image noise of an image generated from scanning the imaging portion based on the setup tube voltage KV, the scout scan condition SC, the scout data SD, and the reference dose ref_mAs under the scan condition of the tube voltage equivalent to the setup tube voltage KV and the dose (mAs) equivalent to the reference dose ref_mAs. The index value NI for an image noise may represent the variance or the standard deviation of pixel values in a tomographic image, for example.

The reference dose specification portion 104 specifies the dose for an imaging target as function f(NI) for the index value NI (see FIG. 3) when an imaging portion is scanned based on the index value NI for an image noise under the scan condition of the tube voltage equivalent to the setup tube voltage KV and the dose (mAs) equivalent to the reference dose ref_mAs.

It is generally known that there is correlative relationship between an image noise level of the acquired image and the imaging target dose when the imaging target is scanned under a predetermined scan condition.

In consideration of this, relation K1 between the index value NI for the image noise and the imaging target dose is previously found for each of tube voltages under the scan condition of the dose (mAs) equivalent to the reference dose ref_mAs. The reference dose specification portion 104 stores the relations K1.

The reference dose specification portion 104 references relation K1 (KV) corresponding to the setup tube voltage KV out of the relations K1. The reference dose specification portion 104 specifies the dose corresponding to the index value NI for an image noise as a dose reference value f(NI) under the scan condition of the tube voltage equivalent to the setup tube voltage KV and the dose (mAs) equivalent to the reference dose ref_mAs.

The relation K1 is found based on dose measurement results after the X-ray CT scan is actually performed on different phantoms, for example. The phantoms are columnar and acrylic and are generally categorized into 16 cm and 32 cm in diameter, for example. The relation K1 may be found through simulation.

The estimated dose calculation portion 105 multiplies the dose reference value f(NI) by a factor and a gain related to the setup dose (mAs) real_mAs to calculate an estimated dose CTDI for the imaging portion when the imaging target is scanned under the scan condition of the tube voltage equivalent to the setup tube voltage KV and the dose (mAs) equivalent to the reference dose ref_mAs.

The estimated dose calculation portion 105 calculates an estimated dose CTDI in accordance with Equation 1, for example.

$$CTDI = f(NI) \cdot \frac{real\_mAs}{ref\_mAs} \cdot gain \qquad \text{Equation 1}$$

In Equation 1, real_mAS/ref_mAs denotes the factor and gain denotes the gain. The gain is used to adjust a calculated dose value as needed. For example, the gain is adjusted and the calculated dose value is adjusted in order to mostly maintain consistency with a dose calculated with the conventional calculation method or the other calculation methods. The X-ray CT apparatus according to the embodiment calculates a dose so as to decrease a difference from a dose calculated on another X-ray CT apparatus under practically the same condition (see FIG. 3).

The CT scan data acquisition portion 106 controls the scanning table 10 and the apparatus gantry 20 and thereby performs CT scan under a predetermined scan condition as the main scan to acquire CT scan data PC. The acquire CT scan is also referred to as projection data.

The image reconstruction portion 107 performs image reconstruction processes such as the filtered back projection based on the CT scan data PC and reconfigures the tomographic image.

The image display control portion 108 controls the monitor 6 and allows a screen of the monitor 6 to display images based on the scout data PS, reconfigured images, and the other information.

The following describes operations of the X-ray CT apparatus according to the embodiment.

Figure 4:
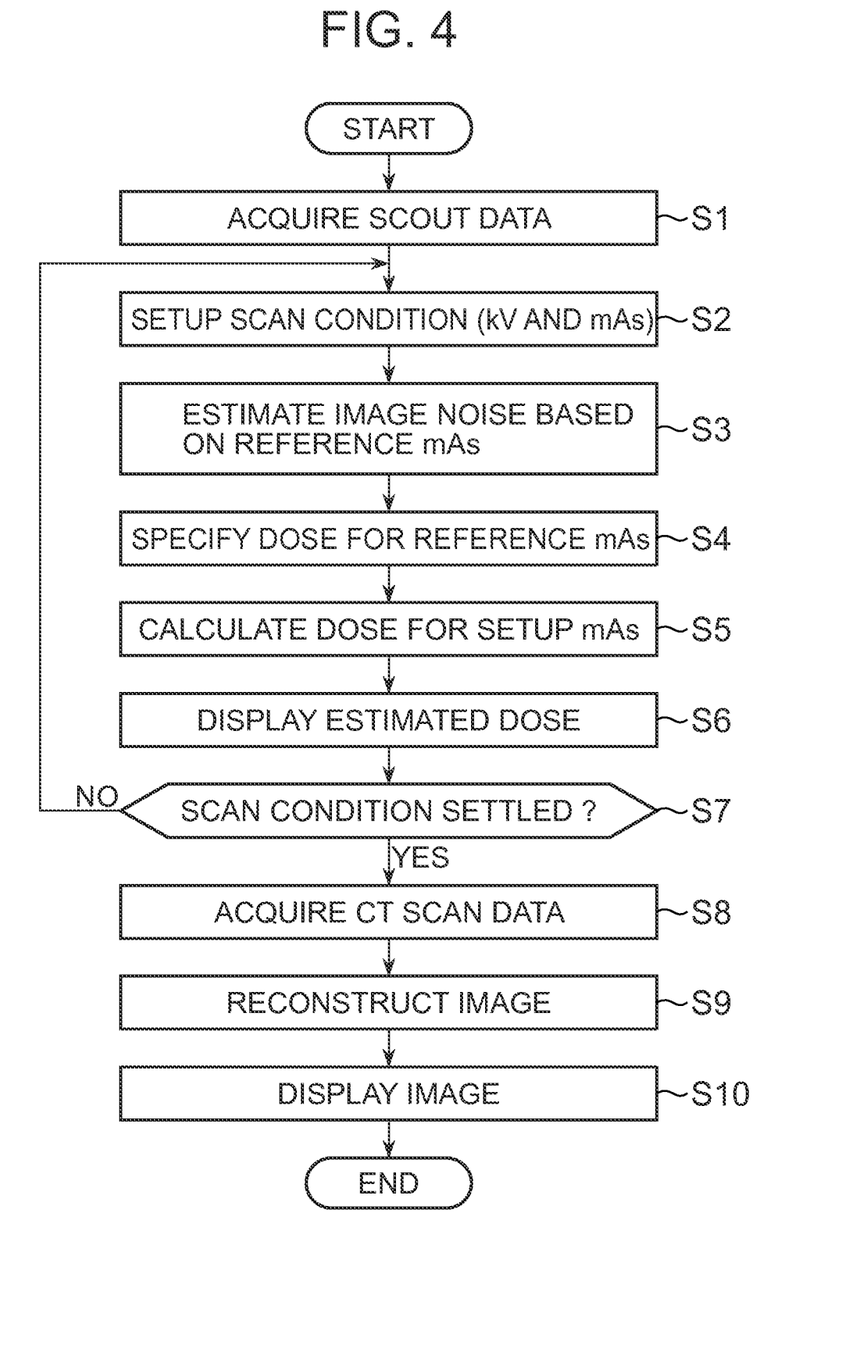
FIG. 4 schematically shows a dose calculation method according to the first embodiment.

FIG. 4 is a flowchart showing a flow of operations on the X-ray CT apparatus according to the embodiment.

At step S1, the scout data acquisition portion 101 controls the scanning table 10 and the scanning gantry 20 to perform scout scan on the subject 40 in accordance with a predetermined scout scan condition SC. The scout data acquisition portion 101 thereby acquires the scout data PS reflecting X-ray absorbing characteristics at an imaging portion. The image display control portion 108 displays a scout image of the subject 40 on the screen of the monitor 6 based on the acquired scout data PS.

At step S2, an operator inputs a scan condition while referencing the scout image. The scan condition setting portion 102 configures the input scan condition as a scan condition for the main scan. The configured scan condition contains the scan range, the setup tube voltage KV, and the setup dose (mAs) real_mAs.

At step S3, the image noise estimation portion 103 uses functions of the CT automatic exposure control to estimate the index value NI for an image noise based on the setup tube voltage KV, the scout scan condition SC, and the scout data SD under the condition of the tube voltage equivalent to the setup tube voltage KV and the dose (mAs) equivalent to the reference dose ref_mAs.

At step S4, the reference dose specification portion 104 references the relation K1 (KV) between the image noise and the dose and specifies the dose reference value f (NI) corresponding to the index value NI for the estimated image noise.

At step S5, the estimated dose calculation portion 105 calculates an estimated dose CTDI for the imaging portion in accordance with the above-mentioned Equation 1 under the scan condition of the setup tube voltage KV and the setup dose (mAs) real_mAs.

At step S6, the image display control portion 108 displays the calculated estimated dose CTDI on the monitor 6.

At step S7, the scan condition setting portion 102 determines whether to settle the scan condition in accordance with operator operations. Control returns to step S2 if the scan condition is not settled and is reviewed. Control proceeds to step S8 if the scan condition is settled.

At step S8, the CT scan data acquisition portion 106 controls the scanning table 10 and the scanning gantry 20, performs X-ray CT scan in accordance with the settled scan condition, and acquires the CT scan data PC. In this example, the X-ray CT scan is assumed to be axial scan but may be assumed to be helical scan. The X-ray CT scan as helical scan needs to take into consideration a helical pitch when the reference dose is specified.

At step S9, the image reconstruction portion 107 performs image reconstruction processes such as the filtered back projection based on the acquired CT scan data PC to reconfigure the tomographic image.

At step S10, the image display control portion 108 displays the reconfigured tomographic image on the screen of the monitor 6.

The first embodiment specifies an index value for the image noise correlative to the dose in accordance with the configured scan condition, references the relationship between the dose and the image noise, and calculates a dose. The embodiment can provide successive or multistage values used as references for the calculation and calculate a dose that more accurately reflects the size of an imaging portion on the subject 40.

(Second Embodiment)

Figure 5:
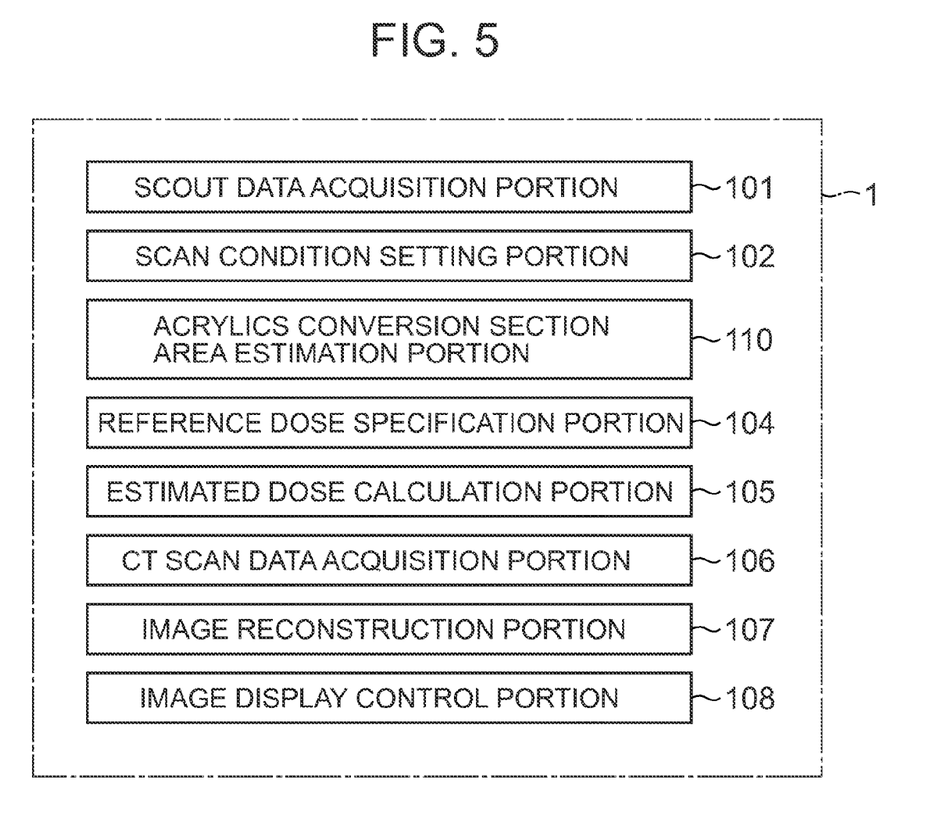
FIG. 5 is a function block diagram showing portions related to scanning performed in the X-ray CT apparatus according to a second embodiment.
Figure 6:
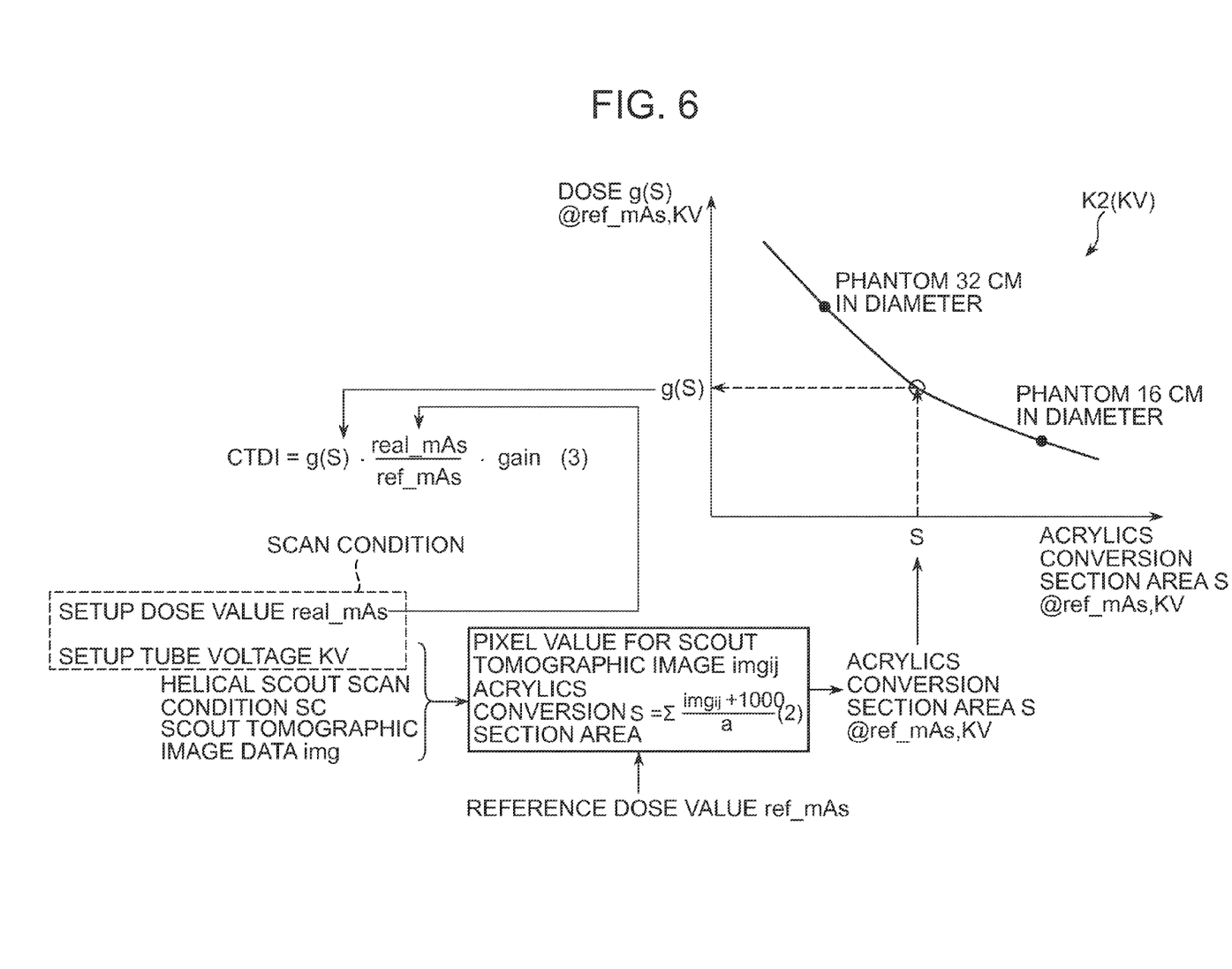
FIG. 6 is a flowchart showing a flow of operations on the X-ray CT apparatus according to the second embodiment.

FIG. 5 is a function block diagram showing portions related to scanning performed in the X-ray CT apparatus according to the embodiment. FIG. 6 schematically shows a dose calculation method according to the embodiment.

The X-ray CT apparatus according to the second embodiment is equivalent to that of the first embodiment as a base except that an acrylics conversion section area estimation portion 110 replaces the image noise estimation portion 103.

The scout data acquisition portion 101 performs low-dose helical scan on an imaging portion of the subject 40 using an X-ray beam with the dose lower than the main scan and acquires scout tomographic image img for the imaging portion.

The acrylics conversion section area estimation portion 110 estimates index value S indicating an acrylics conversion section area of an image generated from scanning the imaging portion under the condition of the tube voltage equivalent to the setup tube voltage KV and the dose (mAs) equivalent to the reference dose ref_mAs. The acrylics conversion section area represents a value resulting from converting the section area of the imaging target into the section area of an acrylic object so as to provide the equal dose under the same condition.

The acrylics conversion section area estimation portion 110 finds the index value S in accordance with Equation 2 based on the setup tube voltage KV, the helical scout scan condition HSC, and the scout tomographic image img. The index value S represents the acrylics conversion section area of the imaging portion under the scan condition of the tube voltage equivalent to the setup tube voltage KV and the dose (mAs) equivalent to the reference dose ref_mAs.

$$S = \sum \frac{img_{ij} + 1000}{a} \quad \text{Equation 2}$$

In Equation 2, $img_{ij}$ denotes a CT value (pixel value) for each pixel in the scout tomographic image img. Parameter a is used for CT value adjustment and varies with the scout tube voltage SV and the setup tube voltage KV contained in the scout scan condition SC. For example, parameter a equals 1100 if the setup tube voltage KV is set to 120 [kV] and the scout tube voltage SV is set to 120 [kV]. That is, the index value S representing the acrylics conversion section area is equivalent to the sum of CT values standardized so as not to vary with a tube voltage in the tomographic image of an imaging portion. It should be noted that the pixel size (scale) is assumed to be always constant.

The reference dose specification portion 104 specifies the dose for an imaging portion as function g (s) of index value S (see FIG. 6) based on the index value S for the acrylics conversion section area when the imaging portion is scanned under the scan condition of the tube voltage equivalent to the setup tube voltage KV and the dose (mAs) equivalent to the reference dose ref_mAs.

It is generally known that there is correlative relationship between an acrylics conversion section area of the acquired image and the imaging target dose when the imaging target is scanned under a predetermined scan condition.

In consideration of this, relation K2 between the index value S for the acrylics conversion section area and the imaging target dose is previously found for each of tube voltages under the scan condition of the dose (mAs) equivalent to the reference dose ref_mAs. The reference dose specification portion 104 stores the relations K2.

The reference dose specification portion 104 references relation K2 (KV) corresponding to the setup tube voltage KV out of the relations K2. The reference dose specification portion 104 specifies the dose corresponding to the index value S for an acrylics conversion section area as a dose reference value g (S) under the scan condition of the tube voltage equivalent to the setup tube voltage KV and the dose (mAs) equivalent to the reference dose ref_mAs.

Similarly to the above-mentioned relation K1, the relation K2 is found based on dose measurement results after the X-ray CT scan is actually performed on CTDI phantoms 16 cm and 32 cm in diameter, for example. The relation K2 may be found through simulation.

The estimated dose calculation portion 105 multiplies the dose reference value g (S) by a factor and a gain related to the setup dose real_mAs to calculate an estimated dose CTDI for the imaging portion when the imaging target is scanned under the scan condition of the tube voltage equivalent to the setup tube voltage KV and the dose (mAs) equivalent to the reference dose ref_mAs.

The estimated dose calculation portion 105 calculates an estimated dose CTDI in accordance with Equation 3, for example.

$$CTDI = g(S) \cdot \frac{real\_mAs}{ref\_mAs} \cdot gain \qquad \text{Equation 3}$$

In Equation 3, real_mAS/ref_mAs denotes the above-mentioned factor and gain denotes the above-mentioned gain. Similarly to Equation 1, the gain is used to adjust a calculated dose value as needed (see FIG. 6).

The following describes operations of the X-ray CT apparatus according to the embodiment.

Figure 7:
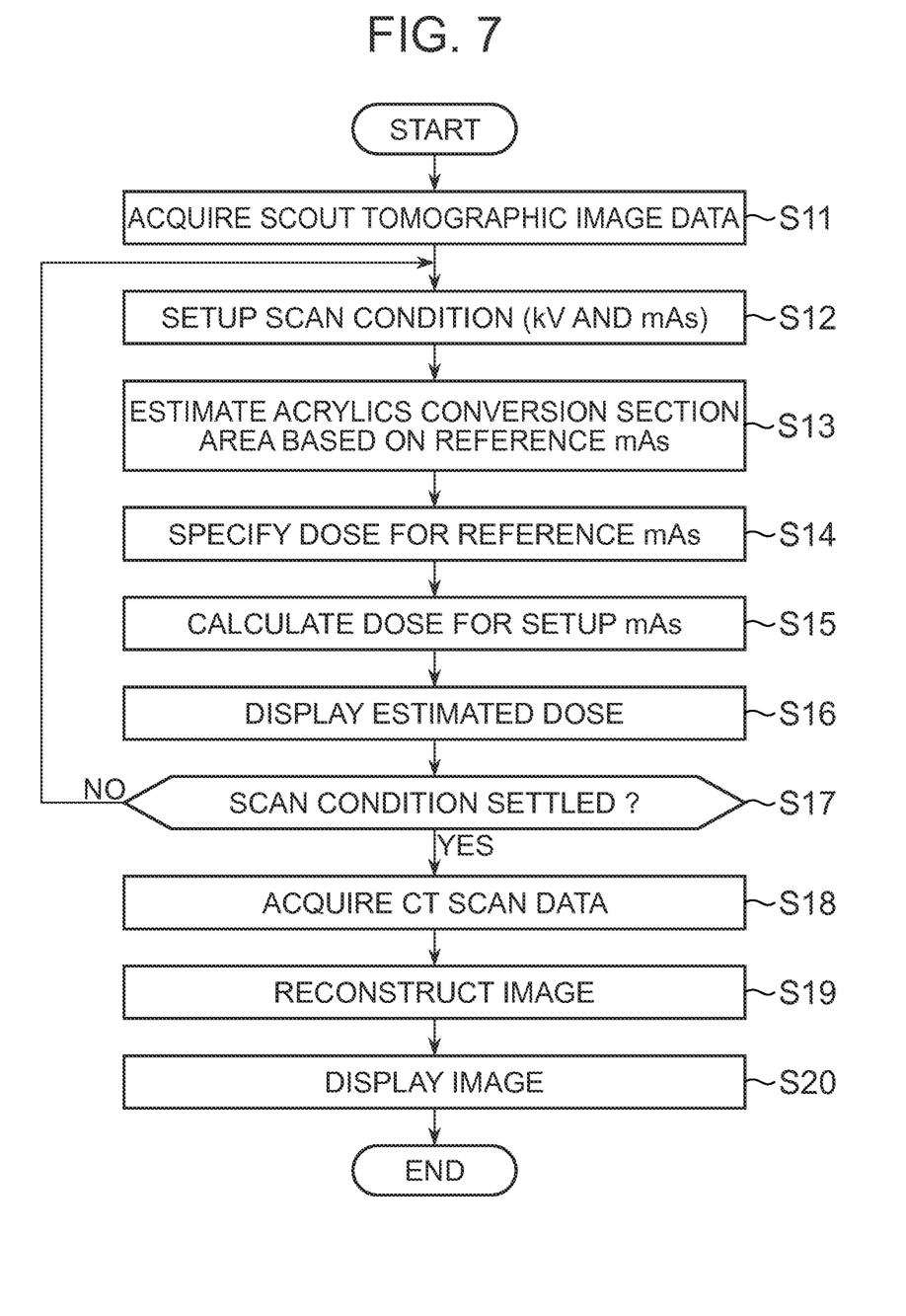
FIG. 7 schematically shows a dose calculation method according to the second embodiment.

FIG. 7 is a flowchart showing a flow of operations on the X-ray CT apparatus according to the embodiment.

At step S11, the scout data acquisition portion 101 controls the scanning table 10 and the scanning gantry 20 to perform low-dose helical scout scan on an imaging portion of the subject 40 in accordance with a predetermined helical scout scan condition HSC. The scout data acquisition portion 101 performs an image reconstruction process on data acquired from the low-dose helical scout scan and generates the scout tomographic image img. The image display control portion 108 overlays the generated scout tomographic image img in the z direction to generate a three-dimensional image. The image display control portion 108 re-projects the image in a predetermined direction and displays the resulting image as a scout image on the screen of the monitor 6.

At step S12, an operator inputs a scan condition while referencing the scout image. The scan condition setting portion 102 configures the input scan condition as a scan condition for the main scan. The configured scan condition contains the scan range, the setup tube voltage KV, and the setup dose (mAs) real_mAs.

At step S13, the acrylics conversion section area estimation portion 110 estimates the index value S for the acrylics conversion section area in accordance with the above-mentioned Equation 2 based on the setup tube voltage KV, the helical scout scan condition HSC, and the scout tomographic image img under the condition of the tube voltage equivalent to the setup tube voltage KV and the dose (mAs) equivalent to the reference dose ref_mAs.

At step S14, the reference dose specification portion 104 references the relation K2 (KV) between the acrylics conversion section area and the dose and specifies the dose reference value g (S) corresponding to the index value S for the estimated acrylics conversion section area.

At step S15, the estimated dose calculation portion 105 calculates an estimated dose CTDI for the imaging portion in accordance with the above-mentioned Equation 3 under the scan condition of the setup tube voltage KV and the setup dose (mAs)real_mAs.

The contents at step S16 and later are practically equal to those at step 6 and later according to the first embodiment and a description is omitted.

The second embodiment specifies an index value for the acrylics conversion section area correlative to the dose in accordance with a predetermined scan condition and calculates the dose with reference to the relation between the dose and the acrylics conversion section area. Similarly to the first embodiment, the second embodiment can provide successive or multistage values used as references for the calculation and calculate a dose that more accurately reflects the size of the subject. The second embodiment is also applicable to an X-ray CT apparatus having no automatic exposure control because the embodiment calculates a dose without using the automatic exposure control functions.

(Third Embodiment)

Figure 8:
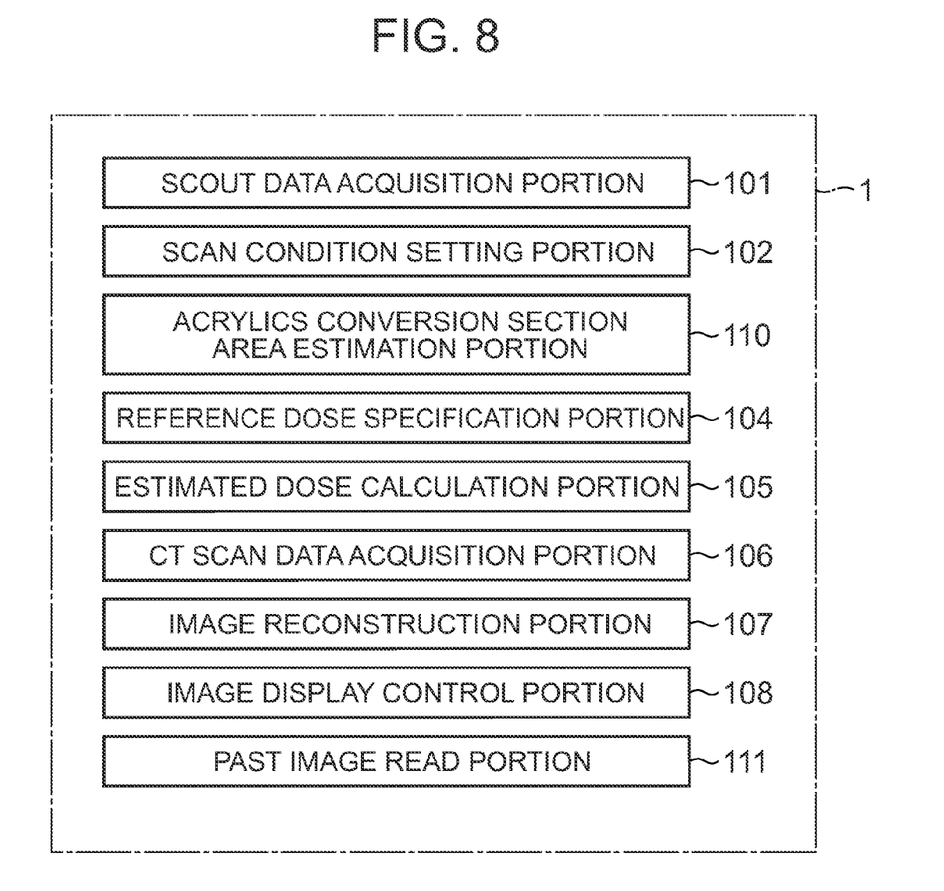
FIG. 8 is a function block diagram showing portions related to scanning performed in the X-ray CT apparatus according to a third embodiment.
Figure 9:
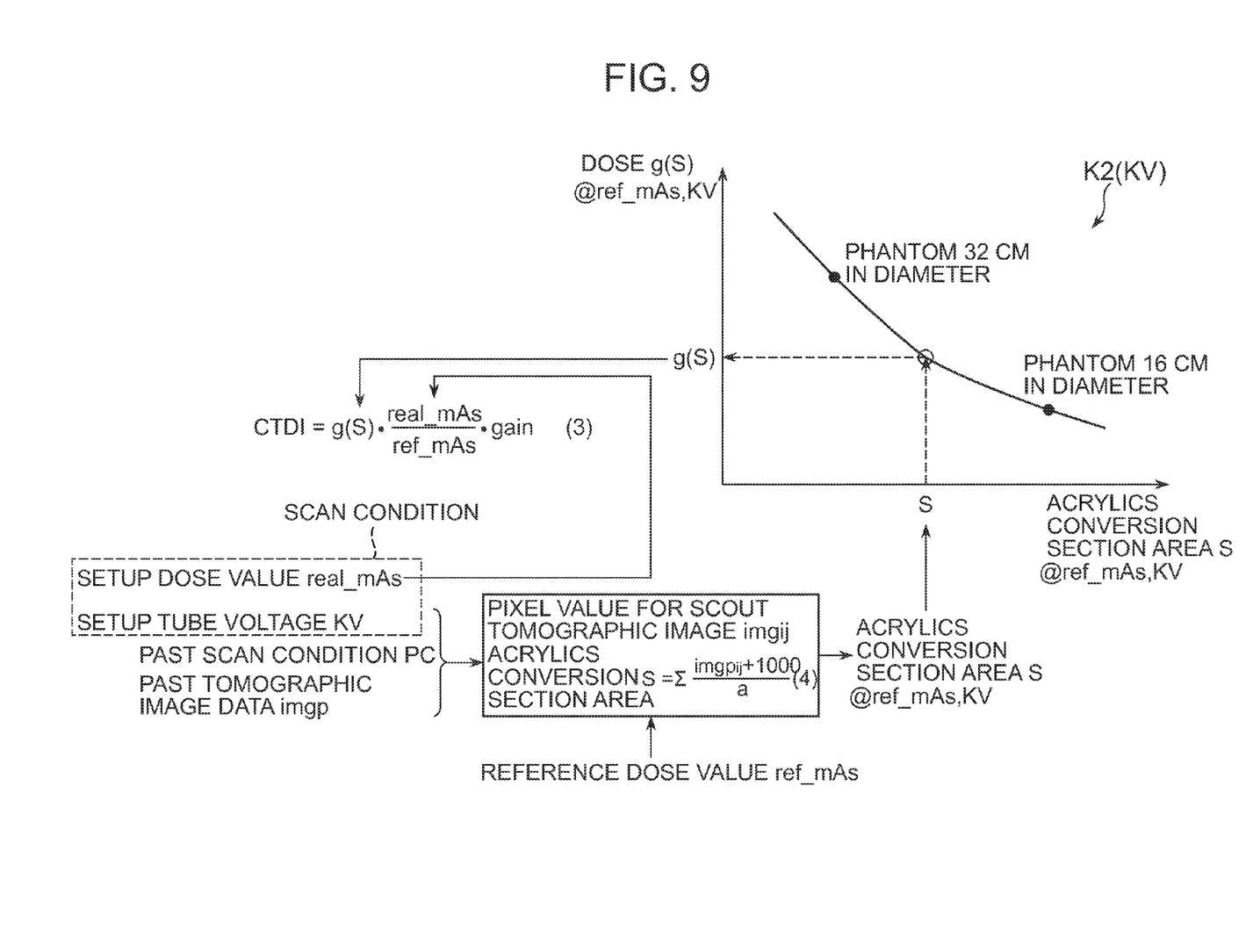
FIG. 9 is a flowchart showing a flow of operations on the X-ray CT apparatus according to the third embodiment.

FIG. 8 is a function block diagram showing portions related to scanning performed in the X-ray CT apparatus according to the embodiment. FIG. 9 schematically shows a dose calculation method according to the embodiment.

The X-ray CT apparatus according to the third embodiment is equivalent to that of the first embodiment as a base except that a past image read portion 111 is added.

A past tomographic image imgp was acquired through scanning practically the same imaging portion on the same subject. The past image read portion 111 reads the past tomographic image imgp from an image database, for example. At this time, the past image read portion 111 also reads a past scan condition PC used for the scan as well as the past tomographic image.

The acrylics conversion section area estimation portion 110 finds the index value S in accordance with Equation 4 based on the setup tube voltage KV, the past scan condition PC, the past tomographic image imgp, helical scout scan condition HSC, and scout tomographic image img. The index value S represents the acrylics conversion section area of the imaging portion under the scan condition of the tube voltage equivalent to the setup tube voltage KV and the dose (mAs) equivalent to the reference dose ref_mAs.

$$S = \sum \frac{imgp_{ij} + 1000}{a}. \qquad \text{Equation 4}$$

In Equation 4, $imgp_{ij}$ denotes a CT value (pixel value) for each pixel in the past tomographic image imgp. Parameter a is used for CT value adjustment and varies with the scout tube voltage SV and the setup tube voltage KV contained in the scout scan condition SC. For example, parameter a equals 1200.

The following describes operations of the X-ray CT apparatus according to the embodiment.

Figure 10:
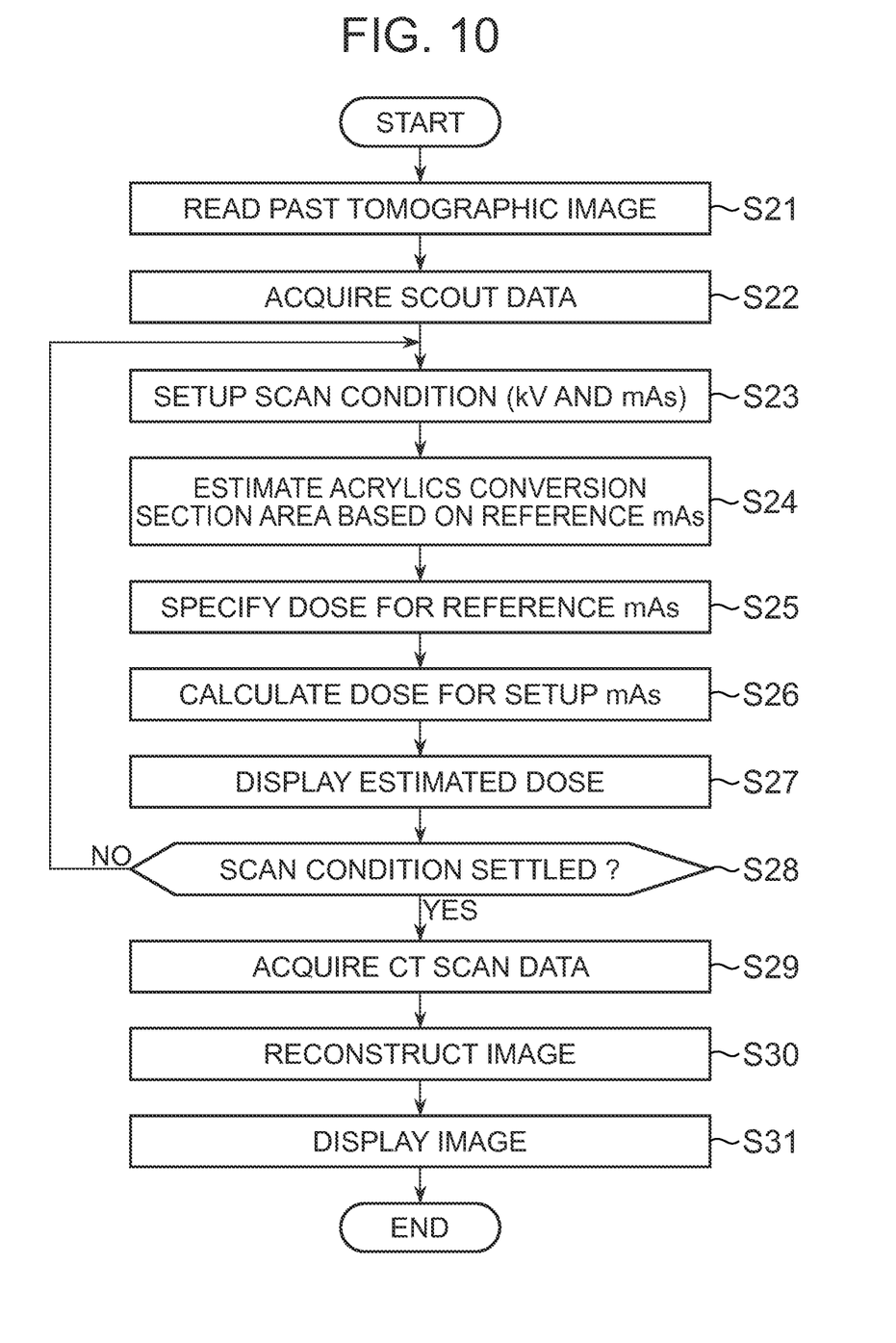
FIG. 10 schematically shows a dose calculation method according to the third embodiment.

FIG. 10 is a flowchart showing a flow of operations on the X-ray CT apparatus according to the embodiment.

At step S31, the past image read portion 111 reads the past tomographic image imgp on the same subject and imaging portion as well as the past scan condition PC from an image database, for example.

At step S32, the scout data acquisition portion 101 controls the scanning table 10 and the scanning gantry 20 to perform scout scan on the subject 40 in accordance with a predetermined scout scan condition SC. The scout data acquisition portion 101 thereby acquires the scout data PS reflecting X-ray absorbing characteristics at the imaging portion. The image display control portion 108 displays a scout image of the subject 40 on the screen of the monitor 6 based on the acquired scout data PS.

At step S33, an operator inputs a scan condition while referencing the scout image. The scan condition setting portion 102 configures the input scan condition as a scan condition for the main scan. The configured scan condition contains the scan range, the setup tube voltage KV, and the setup dose (mAs) real_mAs.

At step S34, the acrylics conversion section area estimation portion 110 estimates the index value S for the acrylics conversion section area in accordance with the above-mentioned Equation 4 based on the setup tube voltage KV, the past scan condition PC, and the past tomographic image imgp under the condition of the tube voltage equivalent to the setup tube voltage KV and the dose (mAs) equivalent to the reference dose ref_mAs.

The contents at step S35 and later are practically equal to those at step 14 and later according to the second embodiment and a description is omitted.

Similarly to the first embodiment, the third embodiment can calculate a dose that more accurately reflects the size of the subject. An estimated dose can be calculated even before the scout scan since the past tomographic image is used to calculate the dose.

It is to be distinctly understood that the present invention is not limited to the above-mentioned embodiments but may be otherwise variously embodied within the spirit and scope of the invention.

For example, the above-mentioned embodiments specify the reference dose using the index value indicative of an image noise or an acrylics conversion section area. Any feature quantity may be available as long as it is associated with a scanned image and is correlative to a dose. The acrylics conversion section area represents a feature quantity appropriate for acrylic phantoms. A non-acrylic phantom may use the conversion section area for its material.

The above-mentioned embodiments calculate and display the CTDI value as a dose per unit length, for example. In some embodiments, values may be calculated and displayed based on other specifications such as a DLP value.

The invention claimed is:

1. An X-ray CT apparatus comprising:
    an acquisition device configured to acquire data representing a tomographic image of an imaging target by performing a pre-scan on the imaging target prior to performing a main scan;
    a setting device configured to set a setup X-ray tube voltage and a setup X-ray dose used for the main scan on said imaging target;
    an estimation device configured to estimate an index corresponding to a value converted into a section area of an object as a section area of the imaging target, wherein the object is made of one of acrylics and other predetermined materials such that the object provides an equal dose for a case where a scan radiating X-ray defined from a predetermined reference dose is performed at the setup X-ray tube voltage, the estimation device configured to estimate the index based on a scan condition used for the pre-scan and the acquired data;
    a specifying device configured to specify a dose corresponding to the estimated index based on a relationship between the estimated index and a dose for the case where the scan radiating X-ray defined from the predetermined reference dose is performed at the setup X-ray tube voltage; and
    a calculation device configured to calculate an exposed dose for the imaging target for a case where the main scan is performed at the setup X-ray tube voltage and the setup X-ray dose, based on the specified dose.

2. The X-ray CT apparatus according to claim 1, wherein the index is a total of standardized pixel values associated with a tomographic image of the imaging target.

3. The X-ray CT apparatus according to claim 2, wherein said estimation device is configured to estimate the index by using the following equation:

the index $=\Sigma[(img_{ij}+1000)/a]$, wherein $img_{ij}$ denotes a CT value for each pixel in the tomographic image, parameter a is used for CT value adjustment and varies with the setup X-ray tube voltage and an additional setup X-ray tube voltage contained in a scan condition used for the pre-scan.

4. The X-ray CT apparatus according to claim 1, wherein the acquired data is obtained from one of a helical scout scan and an axial scout scan on the imaging target.

5. The X-ray CT apparatus according to claim 1, wherein said calculation device is configured to multiply the specified dose and a predetermined gain by a value obtained from dividing the setup X-ray dose by the predetermined reference dose to calculate the exposed dose for the imaging target.

6. The X-ray CT apparatus according to claim 5, wherein the gain is determined such that a difference is decreased between a dose calculated for the X-ray CT scan and a dose calculated for another X-ray CT scan under substantially the same condition.

7. The X-ray CT apparatus according to claim 1, wherein the acquired data is obtained from a past X-ray CT scan of the imaging target.

8. The X-ray CT apparatus according to claim 1, wherein the relationship is obtained from an actual X-ray CT scan performed on a plurality of columnar phantoms each having a different diameter.

9. An X-ray CT apparatus comprising:
    an acquisition device configured to acquire data representing a tomographic image of an imaging target by performing a pre-scan on the imaging target prior to performing a main scan;

a setting device configured to set a setup X-ray tube voltage and a setup X-ray dose used for the main scan on the imaging target;

an estimation device configured to estimate an index corresponding to image noise level on a reconstructed image for a case where a scan radiating X-ray defined from a predetermined reference dose is performed at the setup X-ray tube voltage, the estimation device configured to estimate the index based on a scan condition used for the pre-scan and the acquired data;

a specifying device configured to specify a dose corresponding to the estimated index based on a relationship between the estimated index and a dose for the case where the scan radiating X-ray defined from the predetermined reference dose is performed at the setup X-ray tube voltage; and a calculation device configured to calculate an exposed dose for the imaging target for a case where the main scan is performed at the setup X-ray tube voltage and the setup X-ray dose, based on the specified dose.

10. The X-ray CT apparatus according to claim 9, wherein said estimation device is configured to estimate the index by using a CT automatic exposure control function.

11. The X-ray CT apparatus according to claim 9, wherein the acquired data is obtained from performing a scout scan on the imaging target.

12. The X-ray CT apparatus according to claim 9, wherein said calculation device is configured to multiply the specified dose and a predetermined gain by a value obtained from dividing the setup X-ray dose by the predetermined reference dose to calculate the exposed dose for the imaging target.

13. The X-ray CT apparatus according to claim 12, wherein the gain is determined such that a difference is decreased between a dose calculated for the X-ray CT scan and a dose calculated for another X-ray CT scan under substantially the same condition.

14. The X-ray CT apparatus according to claim 9, wherein the acquired data is obtained from a past X-ray CT scan of the imaging target.

15. The X-ray CT apparatus according to claim 9, wherein the relationship is obtained from an actual X-ray CT scan on a plurality of columnar phantoms each having a different diameter.

16. A non-transitory computer readable medium storing a program that instructs a computer to function as:

an acquisition device configured to acquire data representing a tomographic image of an imaging target by performing a pre-scan on the imaging target prior to performing a main scan;

a setting device configured to set a setup X-ray tube voltage and a setup X-ray dose used for the main scan on said imaging target;

an estimation device configured to estimate an index corresponding to a value converted into a section area of an object as a section area of the imaging target, wherein the object is made of one of acrylics and other predetermined materials such that the object provides an equal dose for a case where a scan radiating X-ray defined from a predetermined reference dose is performed at the setup X-ray tube voltage, the estimation device configured to estimate the index based on a scan condition used for the pre-scan and the acquired data;

a specifying device configured to specify a dose corresponding to the estimated index based on a relationship between the estimated index and a dose for the case where the scan radiating X-ray defined from the predetermined reference dose is performed at the setup X-ray tube voltage; and a calculation device configured to calculate an exposed dose for the imaging target for a case when the main scan is performed at the setup X-ray tube voltage and the setup X-ray dose, based on the specified dose.

* * * * *